United States Patent [19]
Yanai et al.

[11] Patent Number: 5,508,291
[45] Date of Patent: Apr. 16, 1996

[54] FELINE INTERFERON

[75] Inventors: Akira Yanai; Naoko Nakamura; Susumu Matsuda, all of Kamakaura, Japan

[73] Assignee: Toray Industries, Inc., Japan

[21] Appl. No.: 291,597

[22] Filed: Dec. 29, 1988

[30] Foreign Application Priority Data

Dec. 29, 1987 [JP] Japan .................................. 62-336297
Jul. 8, 1988 [JP] Japan .................................. 63-171490
Oct. 18, 1988 [JP] Japan .................................. 63-262057

[51] Int. Cl.⁶ .......................... C07K 14/555; A61K 38/21
[52] U.S. Cl. ........................................... 530/351; 424/85.4
[58] Field of Search ............................ 530/351; 424/85.4

[56] References Cited

U.S. PATENT DOCUMENTS 4,861,720  8/1989  Pederson et al. ........................ 424/89

FOREIGN PATENT DOCUMENTS 0255242  2/1988  European Pat. Off. .

OTHER PUBLICATIONS

Yasuda et al. *Clin. Exp. Immunol* 69: pp. 240–245 (1987).
Yasuda et al *Prep. Biochem* 16(3):217–226 (1986).
Weiss et al. *Am. Journal of Vet. Res* 49(8): 1329–1335 (1988).
*Interferons and their Actions*, Stewart, ed. CRC Press, Inc., Boca Raton, p. 50.
177 USPQ 381 (CCPA 1973) *In. Re. Davies*.
Pestka *Arch of Biochem and Biophy* 221(1):1–37 (1983).
Yamamoto et al, "A Feline Retrovirus Induced . . . ," *Vet. Immunol. and Immunopathol.*, 11 (1986) pp. 1–19.
Yasuda et al, "Partial purification and characterization . . . ," *Prep. Biochem.*, vol. 16, No. 3, 1986.

*Primary Examiner*—Stephen G. Walsh
*Attorney, Agent, or Firm*—Birch, Stewart, Kolasch & Birch

[57] ABSTRACT

Purified feline interferon polypeptides are disclosed. A synthetic plasmid in which DNA encoding protein of a feline interferon is integrated, a transformant obtainable by the transformation of a host cell by the use of the synthetic plasmid and a feline interferon having a biological activity given by a protein carrying a specific amino acid sequence, a feline interferon gene encoding the feline interferon, a feline interferon precursor comprised of a cleavable peptide or a signal peptide being linked to the N terminal of the feline interferon, a feline interferon precursor gene encoding the feline interferon precursor and a method for producing the feline interferon, which are applied to the mass production of a feline interferon to be used as a remedy for feline vital disease and tumor.

4 Claims, 8 Drawing Sheets

```
      10         20         30         40         50
5' TGTGACCTGCCTCAGACCCACGGCCTGCTGAACAGGAGGGCCTTGACGCT
    C   D   L   P   Q   T   H   G   L   L   N   R   R   A   L   T   L 60         70         80         90        100
   CCTGGGACAAATGAGGAGACTCCCTGCCAGCTCCTGTCAGAAGGACAGAA
    L   G   Q   M   R   R   L   P   A   S   S   C   Q   K   D   R   N 110        120        130        140        150
   ATGACTTCGCCTTCCCCCAGGACGTGTTCGGTGGAGACCAGTCCCACAAG
     D   F   A   F   P   Q   D   V   F   G   G   D   Q   S   H   K 160        170        180        190        200
   GCCCAAGCCCTCTCGGTGGTGCACGTGACGAACCAGAAGATCTTCCACTT
    A   Q   A   L   S   V   V   H   V   T   N   Q   K   I   F   H   F 210        220        230        240        250
   CTTCTGCACAGAGGCGTCCTCGTCTGCTGCTTGGAACACCACCCTCCTGG
    F   C   T   E   A   S   S   S   A   A   W   N   T   T   L   L   E 260        270        280        290        300
   AGGAATTTTGCACGGGACTTGATCGGCAGCTGACCCGCCTGGAAGCCTGT
    E   F   C   T   G   L   D   R   Q   L   T   R   L   E   A   C 310        320        330        340        350
   GTCCTGCAGGAGGTGGAGGAGGGAGAGGCTCCCCTGACGAACGAGGACAT
    V   L   Q   E   V   E   E   G   E   A   P   L   T   N   E   D   I 360        370        380        390        400
   TCATCCCGAGGACTCCATCCTGAGGAACTACTTCCAAAGACTCTCCCTCT
    H   P   E   D   S   I   L   R   N   Y   F   Q   R   L   S   L   Y 410        420        430        440        450
   ACCTGCAAGAGAAGAAATACAGCCCTTGTGCCTGGGAGATCGTCAGAGCA
    L   Q   E   K   K   Y   S   P   C   A   W   E   I   V   R   A 460        470        480        490        500
   GAAATCATGAGATCCTTGTATTATTCATCAACAGCCTTGCAGAAAAGATT
    E   I   M   R   S   L   Y   Y   S   S   T   A   L   Q   K   R   L

510
   AAGGAGCGAGAAA
    R   S   E   K
```

FIG. 8

```
             10              20              30              40              50
5' ATGGCGCTGCCCTCTTCCTTCTTGGTGGCCCTGGTGGCGCTGGGCTGCAA
    M   A   L   P   S   S   F   L   V   A   L   V   A   L   G   C   N 60              70              80              90             100
   CTCCGTCTGCTCTCTGGGCTGTGACCTGCCTCAGACCCACGGCCTGCTGA
    S   V   C   S   L   G   C   D   L   P   Q   T   H   G   L   L   N 110             120             130             140             150
   ACAGGAGGGCCTTGACGCTCCTGGGACAAATGAGGAGACTCCCTGCCAGC
      R   R   A   L   T   L   L   G   Q   M   R   R   L   P   A   S 160             170             180             190             200
   TCCTGTCAGAAGGACAGAAATGACTTCGCCTTCCCCCAGGACGTGTTCGG
      S   C   Q   K   D   R   N   D   F   A   F   P   Q   D   V   F   G 210             220             230             240             250
   TGGAGACCAGTCCCACAAGGCCCAAGCCCTCTCGGTGGTGCACGTGACGA
      G   D   Q   S   H   K   A   Q   A   L   S   V   V   H   V   T   N 260             270             280             290             300
   ACCAGAAGATCTTCCACTTCTTCTGCACAGAGGCGTCCTCGTCTGCTGCT
      Q   K   I   F   H   F   F   C   T   E   A   S   S   S   A   A 310             320             330             340             350
   TGGAACACCACCCTCCTGGAGGAATTTTGCACGGGACTTGATCGGCAGCT
    W   N   T   T   L   L   E   E   F   C   T   G   L   D   R   Q   L 360             370             380             390             400
   GACCCGCCTGGAAGCCTGTGTCCTGCAGGAGGTGGAGGAGGGAGAGGCTC
      T   R   L   E   A   C   V   L   Q   E   V   E   E   G   E   A   P 410             420             430             440             450
   CCCTGACGAACGAGGACATTCATCCCGAGGACTCCATCCTGAGGAACTAC
      L   T   N   E   D   I   H   P   E   D   S   I   L   R   N   Y 460             470             480             490             500
   TTCCAAAGACTCTCCCTCTACCTGCAAGAGAAGAAATACAGCCCTTGTGC
    F   Q   R   L   S   L   Y   L   Q   E   K   K   Y   S   P   C   A 510             520             530             540             550
   CTGGGAGATCGTCAGAGCAGAAATCATGAGATCCTTGTATTATTCATCAA
      W   E   I   V   R   A   E   I   M   R   S   L   Y   Y   S   S   T 560             570             580
   CAGCCTTGCAGAAAAGATTAAGGAGCGAGAAA
      A   L   Q   K   R   L   R   S   E   K
```

FELINE INTERFERON

BACKGROUND OF THE INVENTION

This invention relates to a synthetic plasmid and its transformant aiming at mass-producing an interferon (IFN) in which the primary structure of protein is derived from feline genetic information (hereinafter abbreviated to FeIFN) as a medicine (antiviral drug) by gene manipulation technology. This invention further relates to a gene encoding the FeIFN.

An interferon is a physiologically active substance whose main ingredient is a protein showing antiviral activity and is abbreviated to IFN. And, many literatures have been so far published on the interferon, for example, as Literature 1.

By the progress of gene manipulation technology, the mass production of not only a human IFN but also IFNs of animals such as cattle (Literature 2), horse (Literature 3), dog (Literature 3), etc. became possible. As the result, exploitative researches into the use of IFN as remedies for vital disease, cancer, etc. are carried out with respect to some animals (Literature 4).

With respect to experiments in cats, interferon-α, -β and -γ are reported (Literature 5).

However, there has been no report yet that the mass production of a feline IFN is possible by the application of gen6 manipulation.

With respect to cat, it is known that there are many viral diseases including FLTV (Literature 6), feline leukemia, feline viral rhinotracheitis, feline caliciviral disease and feline infectious peritonitis (Literature 7).

In such circumstances, there has been a report on a case in which the life of a cat infected with FeLV was prolonged by the oral administration of human IFN-α or bovine IFN-β (Literature 8). If the IFN is administered not orally but by internal injection, it is readily apprehensive that the production of a neutralizing antibody against a heterologous IFN takes place though a more striking effect is expected. If a homologous IFN, that is, a feline IFN becomes readily available, it is expected that the uses of the feline IFN as an antiviral agent and an antitumor agent for a cat are opened.

SUMMARY OF THE INVENTION

In view of such circumstances as above, the present inventors exerted sought technology for the purpose of mass-producing a FeIFN. That is, they prepared a feline C-DNA library by using a commercially available plasmid vector, from which they successfully isolated a plasmid capable of producing an FeIFN by transient expression in cultured simian cells. Furthermore, they succeeded in preparing an FeIFN-producing Chinese hamster ovary cell by using the plasmid to establish a method for mass-producing an FeIFN simply. Whereby, they completed the present invention.

That is, an object of the present invention is to provide a plasmid making a simian cell express transiently to produce an FeIFN, a transformant of *Escherichia coli* carrying this plasmid, a Chinese hamster cell transformed with this plasmid, an FeIFN obtained from these transformants, an FeIFN gene encoding a specific amino acid sequence, an FeIFN precursor comprised of a cleavable peptide or a signal peptide being linked to the N terminal of the FeIFN, an FeIFN precursor gene encoding the FeIFN precursor and a method for producing the FeIFN.

According to the present invention, the mass production of an FeIFN becomes possible, so that an antiviral agent and an antitumor agent for a cat can be obtained readily.

DETAILED DESCRIPTION OF THE INVENTION

The present synthetic plasmid containing a DNA encoding proteins of an FeIFN can be produced, for example, as follows. That is, poly(A)$^+$ RNA is extracted from cells of a cat to prepare a C-DNA library utilizing a so-called expression plasmid vector by using *Escherichia coli* as a host. From this library, a plasmid having an ability to make a simian COS cell express transiently to produce an antiviral activity can be selected. One of these plasmids having such an activity as above is pFeIFN1 and a transformant *Escherichia coli* carrying pFeIFN1 is *E. coli* (pFeIFN1) whose accession number is FERM BP-1633.

An FeIFN-producing cell obtained by the transformation with the present synthetic plasmid can be produced as follows. In case of a host cell being an eucaryotic cell, the FeIFN-producing cell can be produced, for example, by transfecting a plasmid extracted from the foregoing *E. coli* (pFeIFN1) to a DHFR defective mutant cell of CHO strain derived from a Chinese hamster. In case of a host cell being a procaryotic cell, an FeIFN-producing *Escherichia coli* can be produced, for example, by ligating a DNA encoding protein of an FeIFN with a general *Escherichia coli* expression vector to transform the *Escherichia coli*.

The production of an FeIFN is carried out by incubating the foregoing FeIFN-producing cell.

Hereinafter, the present invention will be described in detail.

With respect to gene manipulation techniques and cell technology techniques, there are many experimentation manuals including Literatures 9 and 10, so that the conventional techniques can be applied.

A C-DNA library prepared according to an ordinary method using reverse transcriptase by making *Escherichia coli* and poll(A)$^+$ RNA extracted from a feline cell act as a host and a substrate respectively.

As a feline cell as a donor of poll (A)$^+$ RNA, for example, an established cultured cell such as LSA (Literature 5) is convenient for use. However, the feline cell to be used in the present invention is not restricted to the LSA. In case of obtaining poll(A)$^+$ RNA from a cultured cell, it is convenient to investigate an interferon inducer suitable for the cell to thereby attempt increasing the yield of IFN mRNA. For example, in case of an LSA cell, the use of NDV (New Castle-disease Virus), TPA (12-O-tetradecanoylphorbol 13-acetate) or the like as an inducer at the time of incubation is advantageous for the increase in the yield of IFN mRNA. As a plasmid vector, it is convenient to use one allowing replication and expression in an animal cell and a replicating ability in *Escherichia coli*, for example, a commercially available plasmid vector such as Okayama-Berg vectors manufactured by Pharmacia Inc. As a host microorganism, *E. coli* K-12 can be used.

The cloning of a plasmid carrying a C-DNA encoding a FeIFN can be carried out by screening a plasmid giving antiviral activity-producing ability to the simian established cell COS1 or COS7 (Literature 18) through the transient expression from a C-DNA library. The transient expression of an FeIFN with a plasmid can be carried out according to ordinary methods such as DEAE-dextran method of Literature 14 and calcium phosphate method of Literature 13. *E. coli* (pFeIFN1) (FERM BP-1633) is an example of a transformant that contains a plasmid which can make COS1 cells produce antiviral activity through the transient expression of FEIFN. The determination of antiviral activity can be carried out by using a feline cultured cell and VSV (Literature 5) and applying ordinary methods such as CPE method described in Literature 12 and the like.

An FeIFN-producing eukaryotic cell can be screened as a transformant having antiviral activity-producing ability from clones transformed to be DHFR-positive by cotransfecting the strain CHO-DUK-XB-11 having a DHFR defective; mutation with a plasmid pFeIFN1 extracted from an *Escherichia coli* transformant of FERM BP-1633 according to an ordinary method such as that of Literature 17, for example, together with a plasmid having DHFR-expressing ability such as pAdD268VA (Literature 20).

Figure 3:
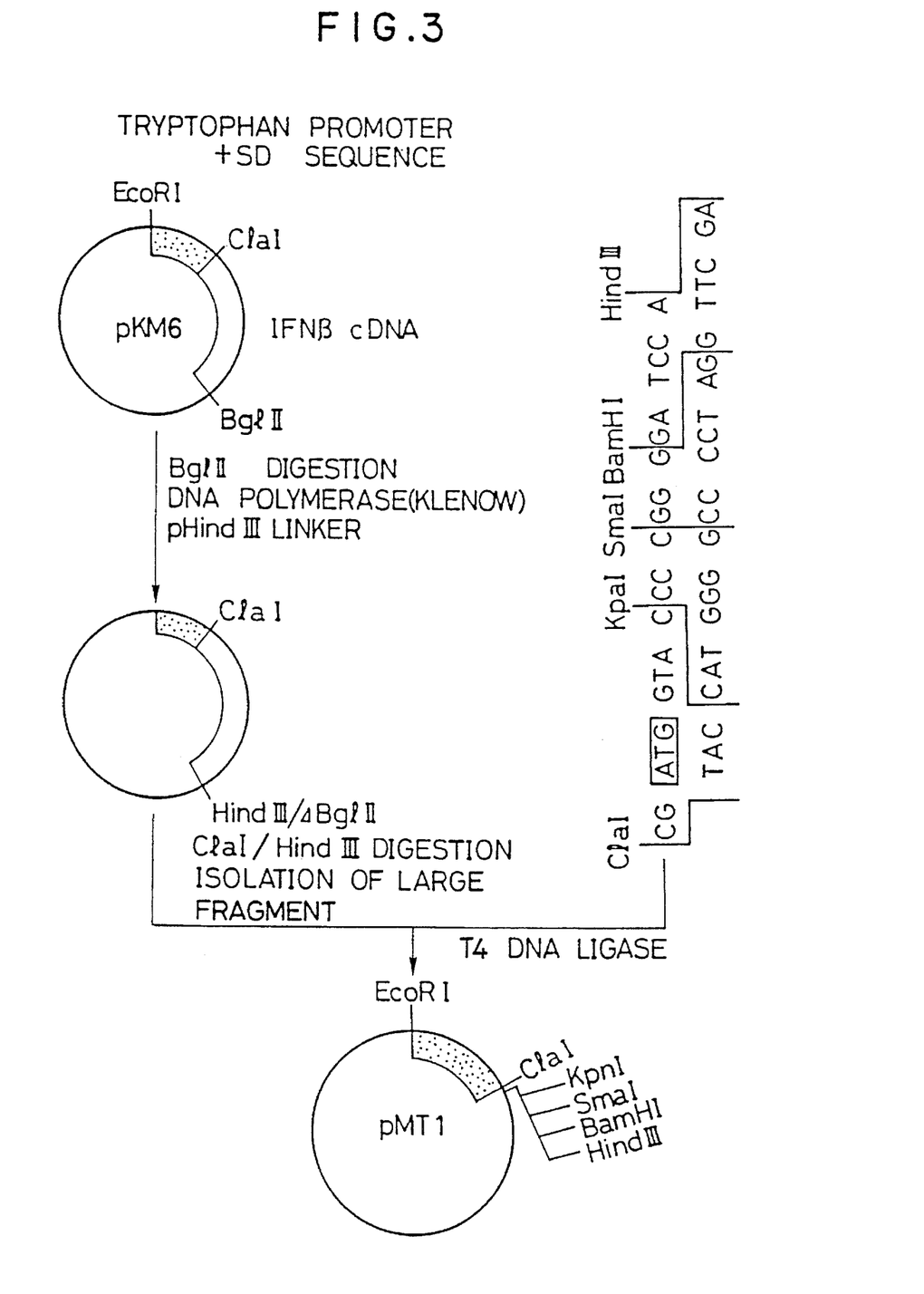

An FeIFN-producing cell of a procaryotic type can be prepared by selecting a transformant having antiviral activity-producing ability from among transformants obtained by transforming *E. coli* K-12 with an synthetic plasmid prepared according to a common gene manipulation of ligating a DNA part encoding protein of an FeIFN, that is, from a plasmid pFeIFN 1, into a so-called expression vector for *Escherichia coli*, for example, PMT1, described in FIG. 3, downstream of the promoter regulating expression of the inserted DNA.

The production of an FeIFN can be carried out by incubating a Chinese hamster transformant CHO-FeIFN (FERM BP-1634) in a medium in which an established CHO cell grows, preferably in a commercially available medium such as MEM-α medium (manufactured by GIBCO Inc., Cat. No. 410-2000) containing 5 to 10% FBS. In case of a transformant being *Escherichia coli*, an FeIFN can be produced by incubating the transformant in an ordinary medium in which *Escherichia coli* proliferates including, for example, LB medium and M9 medium and then disintegrating the bacterial cells. Furthermore, the productivity of an FeIFN can be boosted by the use of an inducer such as indoleacrylic acid for type promoter driven expression or the like.

The produced FeIFN can be purified according to an ordinary method. For example, methods such as affinity chromatography and the like are used preferably. Among those methods, a method using a carrier to which a blue pigment is bonded (hereinafter abbreviated to "blue carrier"), a carrier to which a copper is bonded (hereinafter abbreviated to "copper chelate carrier"), a carrier to which a red pigment is bonded (hereinafter abbreviated to "red carrier") or the like is used particularly preferably. These carriers may be used independently. However, it is preferable to use them in combination in order to increase the purification effect. It is particularly preferable to adopt a method in which blue carrier-using chromatography, copper chelate carrier-using chromatography and red carrier-using chromatography are carried out successively.

As blue carriers, the following are used. The blue pigment is given the general name of CI reactive blue 2. As examples thereof, a blue pigment marketed by Ciba-Geigy under the tradename of "Cibacron Blue F3GA" or "Cibacron Blue 3GA" and the like can be enumerated. As blue carriers to be used in chromatography, blue agarose gels marketed under the tradenames of "Blue Sepharose CL-6B" (Pharmacia Inc.), "Matrex Gel Blue A" (Amicon Inc.), "Affigel Blue" (Biorad Inc.), etc.; blue cellulose gels marketed under the tradenames of "Blue Trisacryl M" (LKB Inc.), "Blue Cellulofine" (Chisso Corp.), etc.; etc. are suitable and readily available.

As the copper chelate carrier, the ones prepared by treating carriers composed of exchangers having chelating ability, e.g., biscarboxymethylamine group [—$N(CH_2COOH)_2$] and the like being bonded to agarose, cellulose, polyacrylamide gel and the like with a solution of copper salt such as copper sulfate and the like can be enumerated. Among these, an isoluble polysaccharide carrier such as "Chelating Sepharose" (manufactured by Pharmacia Inc.) or the like chelated with copper is used preferably.

As the red carrier, the following are used. The red carrier is given the general name of CI reactive red 120. As examples thereof, a red carrier marketed by ICI Inc. under the tradename of "Procion Red HE-3B", etc. can be enumerated. As carriers to which this pigment is bonded, for example, gels marketed under the tradenames of "Red Sepharose C5-6B" (Pharmacia Inc.), "Matrex Gel Red A" (Amicon Inc.), "Red Toyopearl" (Tosoh K.K.), etc. are suitable and readily available.

The purification of an FeIFN according to chromatography is carried out as follows. That is, a solution containing a FeIFN is adsorbed on the above carrier by contact firstly. The adsorption may be done by either batch method or column method. However, the column method can yield higher adsorption efficiency. Then, the adsorbed FeIFN is eluted with an eluent.

The elution of the adsorbed FeIFN from the blue carrier or the red carrier is dependent on the pH value, the ionic strength and the hydrophobicity of an eluent to be used. For example, the adsorbed FeIFN is eluted at pH 6 to 7 at a higher ionic strength. The ionic strength can be increased by raising the concentration of a buffer such as phosphate buffer, acetate buffer, citrate buffer, borate buffer or the like or by the addition of a neutral salt such as sodium chloride, potassium chloride or the like (0.2 to 1.0M). In case of an eluent containing a solvent such as ethylene glycol, propylene glycol or the like that weakens the hydrophobic interaction, the elution at pH 5 to 7 becomes possible.

The elution of the adsorbed FeIFN from the copper chelate carrier is usually carried out with an acidic buffer such as phosphate buffer, acetate buffer, citrate buffer or the like preferably below pH 5. However, the elution at a much higher pH becomes possible at a higher ionic strength.

The composition, the concentration and the amount of an eluent is not restricted particularly. That is, a composition effective for removing impure proteins contained in a crude FeIFN, a concentration required to maintain the pH and the amount of an eluent required to substantially recover the adsorbed FeIFN are employed.

EXAMPLES

Hereinafter, the present invention will be described more specifically, referring to examples.

EXAMPLE 1

(1) Preparation of Feline C-DNA Library

A feline cell LSA-D4-K17 (Literature 5) as a donor of poly (A)$^+$ RNA was proliferated by spinner culture in 200 ml of MEM-L15 medium (50% Eagle's MEM—50% Leibovitz medium) containing 10% FBS. When the cell concentration reached $10^5$ to $10^6$/ml, TPA (12-O-tetradecanoylphorbol 13-acetate manufactured by Sigma Chemical Co.) was added to a final concentration of 5 ng/ml. After continuing the incubation for an additional 20 hours, the cells were harvested by centrifugation. From the harvested cells, poly(A)$^+$ RNAs were extracted by a modification of guanidiumthiocyanate method described in Literature 15. That is, 3 to $5\times10^8$ cells were suspended in 20 ml of 5 mM sodium citrate-0.5% sodium sarkosyl-0.1M mercaptoethanol-6M guanidinethiocyanate and then homogenized by passage of the suspension through an 18G injection needle 10 times. After pouring ⅓ vol. of 0.1M EDTA (pH 7.5)-5.7M CsCl into a polyallomer centrifuge tube, the cell homogenate was layered thereon. The tube and contents were then centrifuged at 35,000 rpm at 20° C. for 20 hours in a Hitachi RPS40T rotor. RNA fractions packed at the bottom of the tube were dissolved in 1 ml of TE (10 mM Tris.HCl-1 mM EDTA, pH 7.5). After mixing the solution with 0.1 ml of 3M sodium acetate solution, the solution was further mixed with 2.5 vol. of cold ethanol and then allowed to stand at −20° C. for 2 hours. A pellet formed at the bottom of the tube by centrifugation was dissolved in 1 ml of TE, incubated at 65° C. for 4 minutes and then ice-cooled. After adding 1 ml of TE to the pellet treated as above, equivalent volume of 1.0M NaCl was mixed thereinto. The resultant mixture was passed through a column packed with 0.5 ml of oligo(dT) cellulose (Type 3, manufactured by Collaborative Research Inc.) equilibrated with 0.5M NaCl-TE to make poly(A)$^+$ RNAs adsorb on the column. After washing the column with 10 ml of 0.5M NaCl-TE, the adsorbed poly(A)$^+$ RNAs were eluted with 5 ml of TE. The poly(A)$^+$ RNAs pelleted according to the ethanolic precipitation method were dissolved in 30 µl of TE and preserved at −80° C. From $2\times10^8$ cells 300 µg of poly(A)$^+$ RNA were obtained. The connection of a poly(A)$^+$ RNA to a plasmid vector and the synthesis of C-DNA were carried out by using commercially available plasmid primers and linkers in the light of Literature 14. That is, 5 µl of 5 mg/ml poly(A)$^+$ RNA was poured into a 1.5 mL Eppendorf tube, to which water was then so added that the total volume might reach 20 µl. After incubating the resultant solution at 65° C. for 3 minutes, the incubated solution was equilibrated to room temperature. To this incubated solution, were added 4 µl of 0.3M Tris.HCl buffer (pH 8.3)-80 mM MgCl$_2$-0.3M KCl-3 mM dithiothreitol, 2 µg (3 µl) of oligo(dT)-tailed pcDV1 plasmid primer (manufactured by Pharmacia Inc.), 4 µl of mixture of each 25 mM dATP, dTTP, dGTP and dCTP, 2 µl of [α-$^{32}$P]dCTP, 3 µl of water and 4 µl of 18 unit/µl reverse transcriptase (manufactured by Seikagaku Kogyo K.K.) in order. Thus prepared solution was incubated at 42° C. for 1 hour to carry out the enzymatic reaction. After terminating the reaction by the addition of 4 µl of 0.25M EDTA and 2 µl of 10% SDS, phenol-chloroform extraction was carried out. 40 µl of 4M ammomium acetate and 160 µl of ethanol was added to the separated aqueous layer after phenol-chloroform extraction procedure, which was then cooled in dry ice for 15 minutes. Thus treated aqueous layer was equilibrated to room temperature and then centrifuged in a microcentrifuge for 10 minutes. After decanting the supernatant, the pellet was dissolved in 20 µl of water. To this solution, were added 20 µl of 4M ammonium acetate and 80 µl of ethanol to carry out the ethanol precipitation again. The resultant pellet was washed with ethanol, dried and then dissolved in 10 µl of water.

To this solution, were added 2 µl of 1.4M sodium cacodylate-0.3M Tris-HCl buffer (pH 6.8)-1 mM dithiothreitol, 1 µl of 200 µg/ml polyadenylic acid (manufactured by Seikagaku Kogyo K.K.),. 1 µl of 20 mM CoCl$_2$, 1.4 µl of 1 mM dCTP, 0.5 µl of 400 Ci/mmol [α-$^{32}$P]dCTP in order. After making the total volume of the solution reach 20 µl by adding water, 0.8 µl of 27 unit/µl terminal nucleotidyl transferase was added thereto. The mixture solution was incubated at 37 µl for 5 minutes and the enzymatic reaction was terminated by placing the culture in ice. The number of dCMP residue added to the 3' end of the DNA was calculated to be 12, on average according to Literature 14. From the reaction solution, nucleic acids were recovered according to phenol-chloroform extraction method and double ethanol precipitation method.

The nucleic acids were dissolved in 40 µl of 10 mM Tris.HCl (pH 8.0)-60 mM NaCl-10 mM MgCl$_2$-1 mM 2-mercaptoethanol solution, to which 10 units of Hind III restriction enzyme was added. After incubating thus prepared solution at 37° C. for 3 hours, DNAs were recovered by the phenol-chloroform extraction and double ethanol precipitation. The recovered DNAs were washed with ethanol, dried and then dissolved in 10 µl of TE buffer.

To this solution, 5 µl of 2M NaCl, 81 µl of TE buffer and 4 µl of commercially available 3'-oligo(dG)-tailed pL1 linker (manufactured by Pharmacia Inc.) were added in order. After heating the mixture solution firstly at 65° C. for 5 minutes and then at 42° C. for 1 hour, this solution was ice-cooled. To the ice-cooled solution, 100 µl of 0.2 mM Tris.HCl buffer (pH 7.5)-40 mM MgCl$_2$-0.1M ammonium sulfate- 1M KCl, 7 µl of 14 mM β-NAD, 50 µl of 1 mg/ml bovine serum albumin solution and 6 µl of 1 mg/ml E. coli DNA ligase were added in order, to which water was so added that the total volume might reach 1 ml. The resultant solution was incubated overnight at 12° C.

To this reaction solution, 2 µl of mixed solution of each 25 mM dATP, dGTP, dTTP and dCTP, 3 µl of 14 mM β-NAD, 0.7 µl of 35 unit/µl E. coli DNA polymerase (manufactured by Takara Shuzo Co., Ltd.), 2.4 µl of 2.5 units/µl E. coli RNase H (manufactured by Takara Shuzo Co., Ltd.) and 4 µl of 1 mg/ml E. coli DNA ligase were added in order. After incubating thus prepared solution firstly at 12° C. for 1 hour and then at 25° C. for 1 hour, the reaction solution was preserved at −20° C.

After carrying out the transformation reaction by adding 100 µl of the preserved reaction solution to 1 ml of suspension of E. coli MC1061 (Literature 16) which was made to be competent according to the method of Literature 15, this reaction solution was poured into 250 ml of LB medium containing 100 µg /ml ampicillin and then incubated overnight at 37° C. To 10 ml of this culture, 0.7 ml of DMSO was added. This portion was preserved at −80° C. as a cDNA library.

(2) Cloning

A portion of thus prepared cDNA library solution was so spread on ten 9-cm diam. LB plates that 1,000 to 2,000 colonies might be formed in each plate. After incubating these plates overnight at 37° C., the grown colonies were scraped off in every petri dish and respectively suspended in each 10 ml of LB media. 3 ml of this suspension was mixed with 0.21 ml of DMSO and then cryopreserved. The remaining suspensions were respectively mixed with each 100 ml of LB media each containing 100 µg/ml ampicillin and then incubated overnight at 37° C. Cells were harvested from respective culture media, and plasmids were extracted and purified from the harvested cells according to the method of Literature 17. Each 30 μg of these plasmids were subjected to the transient expression of COS1 cells proliferated to the confluent state in 9 cm petri dishes by applying the DEAE dextran-transfection method of Literature 14, whereby the FeIFN-producing ability of respective plasmid DNA samples was determined.

That is, after proliferating COS1 cells to the confluent state in 20 ml of RPMI1640 (manufactured by GIBCO Inc.) medium containing 10% FBS in a 9 cm diam. petri dish, the medium was removed therefrom and then 4 ml of RPMI1640 medium containing 5 μg/ml plasmid DNA sample, 50 mM Tris.HCl buffer (pH 7.4), 400 μg/ml DEAE-dextran (manufactured by Pharmacia Inc.) was poured in the petri dish to continue the incubation at 37° C. for 4 hours. The medium was exchanged with 4 ml of RPMI1640 containing 150 μM chloroquine. After a 3-hour incubation at 37° C., the medium was further exchanged with an RPMI1640 medium containing 10% FBS. After the incubation at 37° C. for 3 days, the antiviral activity in the medium was determined. All of the RPMI1640 media mentioned above were used by adding 100 unit/ml penicillin and 100 μg/ml streptomycin.

As the result, 3 out of 10 culture media showed antiviral activity of 20 unit/ml or more, so that the concerned cryopreserved cDNA library solutions were screened for *Escherichia coli* carrying a plasmid giving antiviral activity-producing ability to the COS1 cell in the following manner.

That is, 1 out of 3 cryopreserved cDNA library solutions carrying plasmids producing the activity was diluted, so spread on 10 LB plates each containing 100 μg/ml ampicillin that approx. 600 colonies might be formed per plate and then incubated overnight at 37° C. After preparing replicas thereof as preservation plates, cells were scraped off in every plate, suspended in each 5 ml of LB media and then mixed with each 100 ml of LB media respectively containing 100 μg/ml ampicillin. After incubating thus treated cells overnight at 37° C., the resultant cells were harvested to extract and purify plasmids therefrom. Each 20 μg per petri dish of these 10 kinds of plasmids were subjected to the transient expression of COS1 cells according to the DEAE-dextran method, whereby the FeIFN-producing ability was determined.

As the result, 1 out of 10 plasmid samples were recognized to have the FeIFN-producing ability, so that 593 colonies in the concerned preservation plate were transplanted to fresh LB plates containing ampicillin by using tooth picks in the ratio of approx. 100 colonies per fresh plate. After an overnight incubation at 37° C., cells scraped off from every plate and then incubated overnight in each 100 ml of ampicillin containing-LB medium. From the harvested cells, plasmids were extracted and purified. The antiviral activity-producing ability of each plasmid was determined according to the transient expression method.

As the result, one plasmid sample was recognized to have the antiviral activity-producing ability, so that each 100 colonies of the concerned preservation plate were incubated in each 2 ml of LB medium. From these media, plasmids were extracted. The antiviral activity-producing ability of each extracted plasmid was determined according to the transient expression method. A plasmid having the highest antiviral activity-producing ability and an *Escherichia coli* carrying the plasmid were resepctively designated as pFeIFN1 and *E. coli* (pFeIFN1), and this strain was deposited in the Fermentation. Research Institute (FERM BP-1633).

(3) Method for Antiviral Activity Determination

The antiviral activity was determined by using Vesicular Stomatitis Virus as a virus and a feline Fc9 cell (Literature 5) as a sensitive cell according to CPE method. As a standard reference, an HuIFN-α calculated in terms of NIH's human natural αIFN was used.

(4) FeIFN Production by CHO Cell

A CHO cell strain DUK-XB-11 (Literature 18) as a DHFR defective mutant, which was subcultured at a dilution rate of 1/10 in a 12-well plate by using MEMα medium (manufactured by GIBCO Inc., Cat. No. 410-1900) containing 10% FBS and then cultured for 3 days, was cotransfected with 5 μg of pFeINF1 and 0.5 μg of pAdD26SVA carrying a DHFR gene (Literature 20) by applying the calcium phosphate method of Literature 13. After a 1-day incubation, the culture was transplanted to a selective medium of nucleic acid constituent-free MEMα (manufactured by GIBCO Inc., Cat. No. 410-2000) containing 10% FBS. In the course of incubation, the medium was exchanged twice. After a 10-day incubation in a 9 cm diam. petri dish, 147 colonies were obtained. From among these colonies, 16 colonies were transplanted to 24-well plates and then incubated for 3 to 4 days until the plates became confluent. As a result of determining the antiviral activity of the culture media, 8 culture media were recognized to have an activity of 10,000 unit/ml or more. Active clones were purified according to the single colony isolation method. One of the purified colonies was designated as CHO-FeIFN and deposited on Dec. 23, 1987 in the Fermentation Research Institute, 1–3, Higashi 1-chome, Tsukuba-shi, Ibaraki-ken 305, JAPAN (FERM BP-1634).

Culture medium containing $2.8 \times 10^4$ U/ml of feline interferon was adjusted to pH 2.0 by the addition of 3 ml of 0.1N HCl to 5 ml of the medium. The mixture was incubated at 4° C. for 24 hours or 10 days. After incubation, 1 ml of the sample was removed and centrifuged. The supernatant was tested for feline interferon activity. The feline interferon activity following 24 hour incubation was $1.8 \times 10^4$ U/ml (103% of original activity), while the activity of the 10-day incubation was $1.7 \times 10^4$ U/ml (97% of original activity. The feline interferon activity was calculated after adjusting the volume.

(5) pFeIFN1

Figure 1:
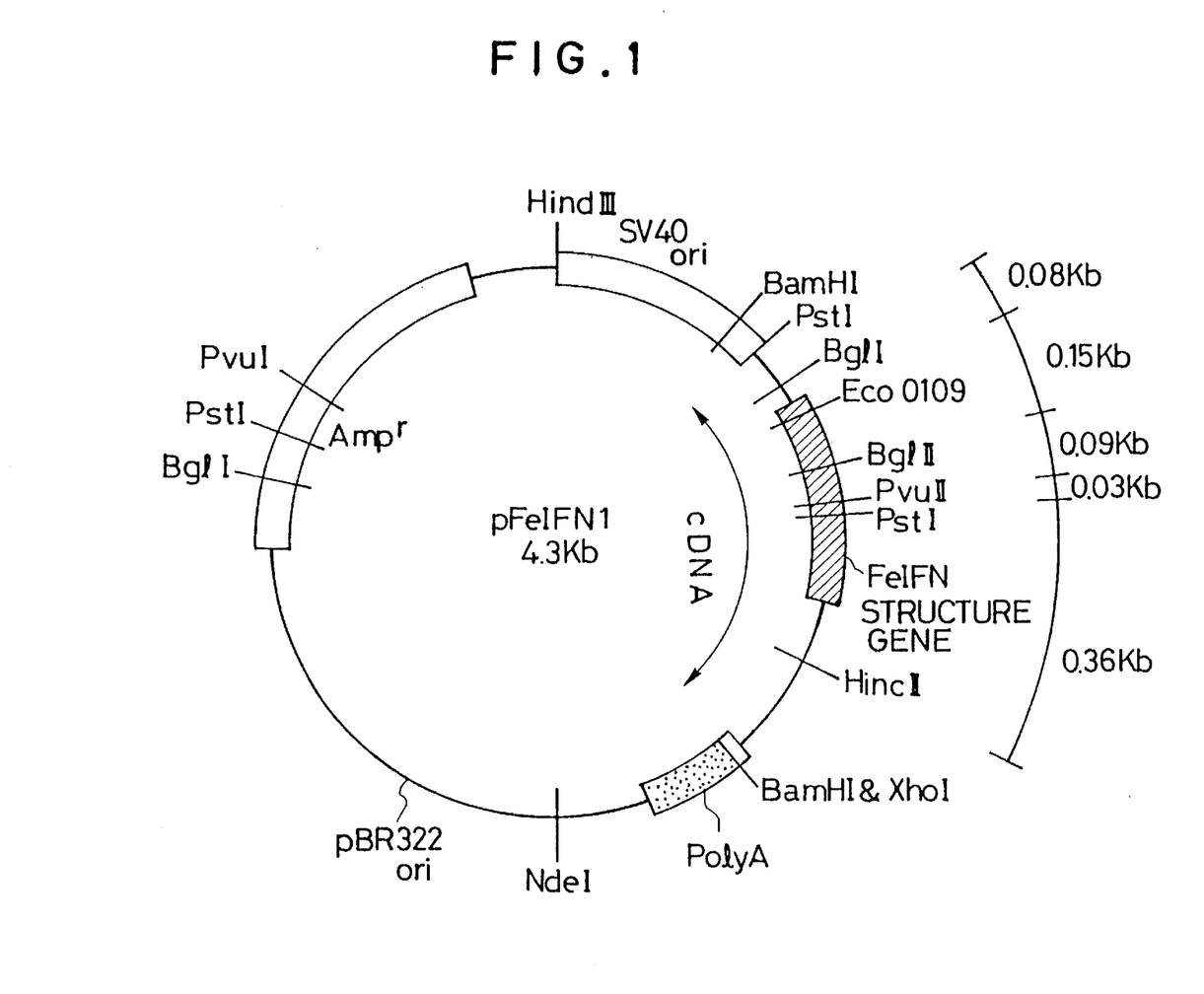
FIG. 1 shows a restriction map of a synthetic plasmid pFeIFN 1 according to the present invention.

The pFeIFN1 has a size of 4.3 Kb, and the restriction map thereof is shown in FIG. 1.

EXAMPLE 2

(1) Preparation of a Fragment Including FeIFN Structure Gene

Figure 2:
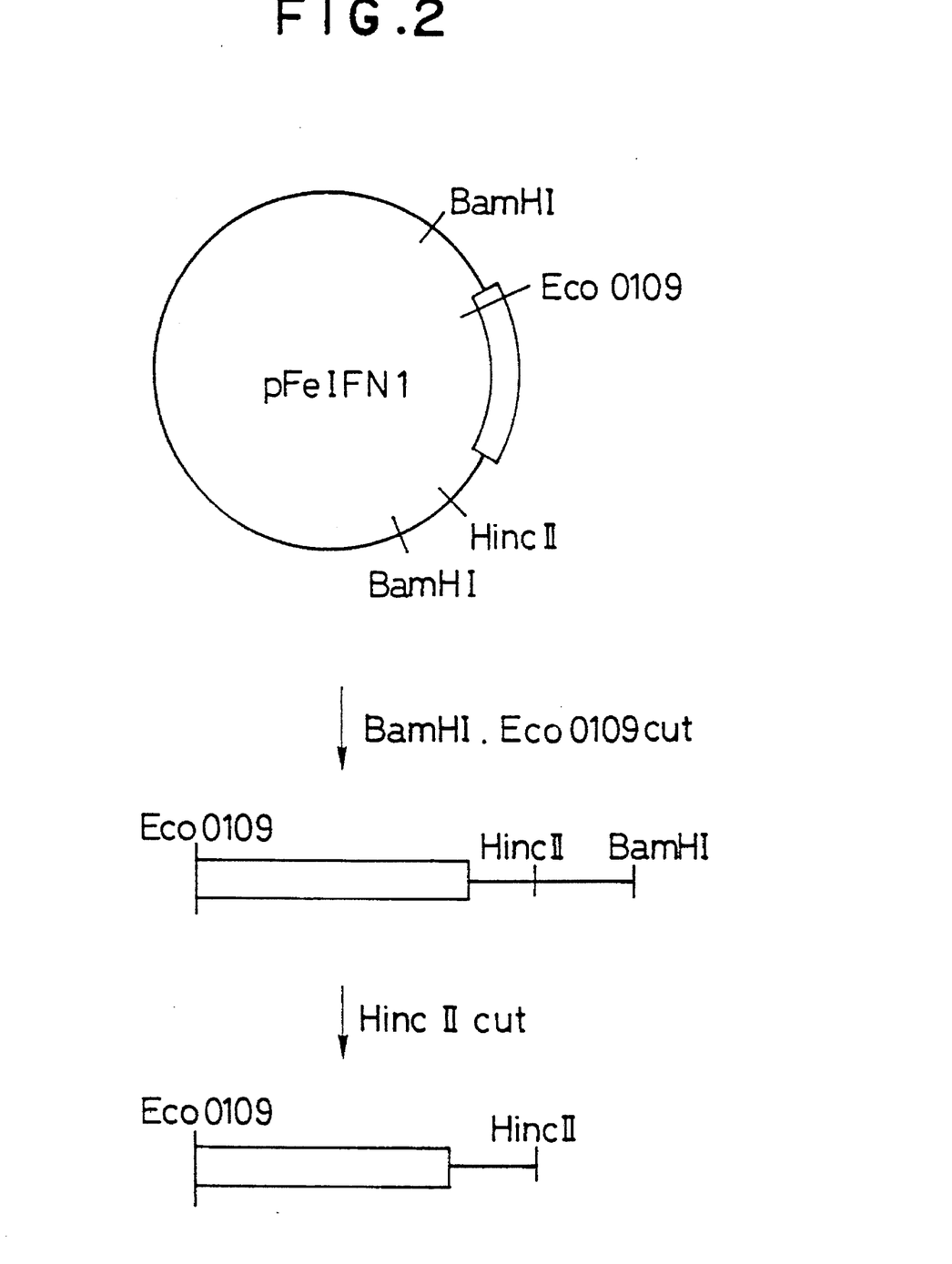
FIGS. 2 to 6 show preparation procedures for an expression plasmid pFeIFN 2 for *Escherichia coli* according to the present invention.

From the plasmid pFeIFN1 shown in FIG. 1, the fragment containing a part of FeIFN structure genes was prepared according to the method shown in FIG. 2.

That is, 100 μg of plasmid pFeIFN1 was completely digested with the restriction enzymes BamHI and Eco0109. The resulting DNA fragments were separated by agarose gel electrophoresis and the DNA fragment of approx. 1 Kb was extracted by electroelution to recover approx. 20 μg of DNA fragment.

Then, the recovered 20 μg of DNA fragment was completely deposited with the restriction enzyme HincII. Among the obtained DNA fragments, those of approx. 630 bp were treated in the same manner as above to recover approx. 15 μg of DNA fragment. In such manners as above, Eco0109-HincII fragment containing a downstream part of FeIFN to the Eco0109 site was obtained.

(2) Preparation of Plasmid pMT1

A vector pMT1 which has SD sequence required for translation downstream from a tryptophan promoter and into which a synthetic oligomer containing the translation initiation codon ATG and a recognition site for 5 kinds of restriction enzymes were inserted downstream to the SD sequence was prepared.

After digesting a human interferon-β expression plasmid pKM6 (Jap. Pat. Appln. Laid-open No. 19487/1986) with BglII, the digested site was made to be a blunt end with an E. coli DNA polymerase I large fragment (Klenow) enzyme. A pHindIII linker, i.e., d(pC-A-A-G-C-T-T-G) was ligated to the blunt end. After digestion with ClaI and HindII, the larger fragment was separated by agarose gel electrophoresis.

On the other hand, 2 pieces of oligomers, each of which was so designed that it might contain a translation initiation codon ATG, ClaI site at 5'-end, HindIII site at 3'-end and KpnI, SmaI and BamHI sites inside and were synthesized according to the solid phase method, were heated at 60° C. for 5 minutes and then gradually cooled so as to anneal them. The larger fragment and the synthesized fragment were ligated with a T4 DNA ligase to obtain pMT1.

(3) Preparation of ClaI-SmaI fragment from pMT1

Figure 4:
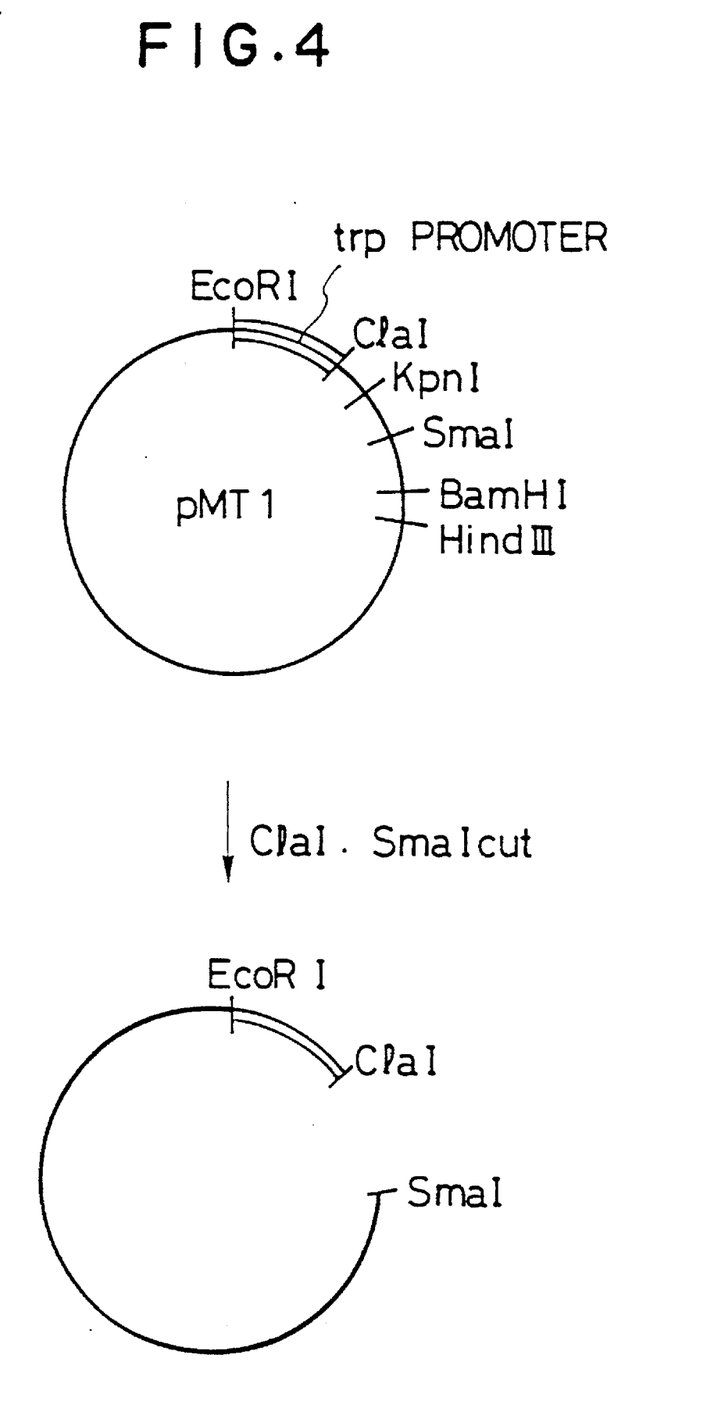

As shown in FIG. 4, 50 μg of plasmid pMT1 was completely digested with restriction enzymes ClaI and SmaI end, subjected to agarose gel electrophoresis to remove smaller DNA fragments. As the result, approx. 40 μg of the desired DNA fragment was recovered to obtain ClaI-EcoRI fragments containing a tryptophan promoter as an E. coli expression promoter.

(4) Preparation of ClaI-EcoRI Fragment at N Terminal

This part was synthesized on the basis of the results of the determination of base sequences of DNA on the upstream of Eco0109 site in an FeIFN structural gene integrated in the plasmid pFeIFN1.

Figure 5:
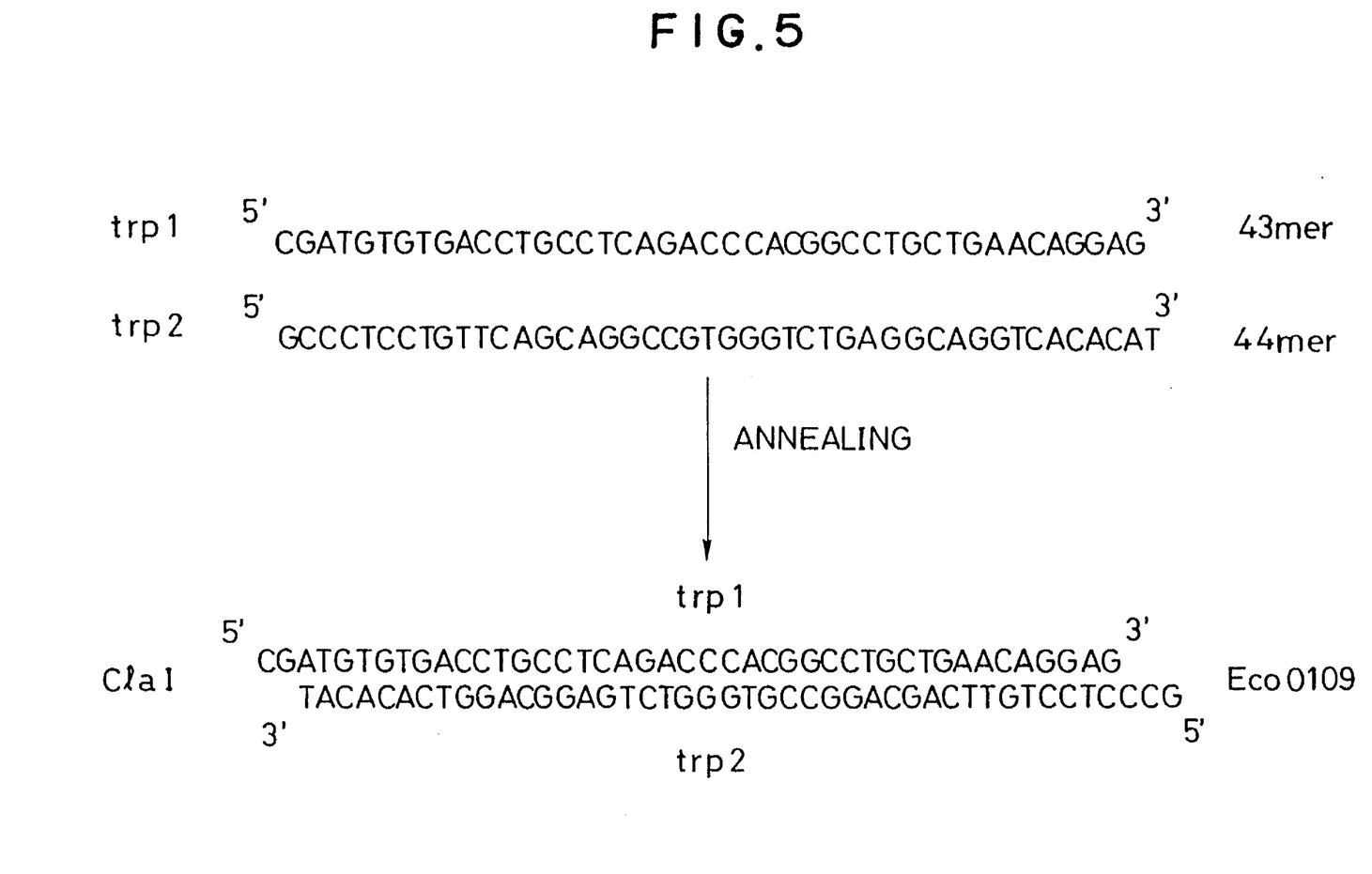

That is, a DNA fragment which contains initiation codon ATG at its N terminal, ClaI site next to the initiation codon and Eco0109 site was synthesized by annealing 43 mer and 44 mer synthetic DNAs as shown in FIG. 5.

(5) Preparation of Plasmid pFeIFN2

Figure 6:
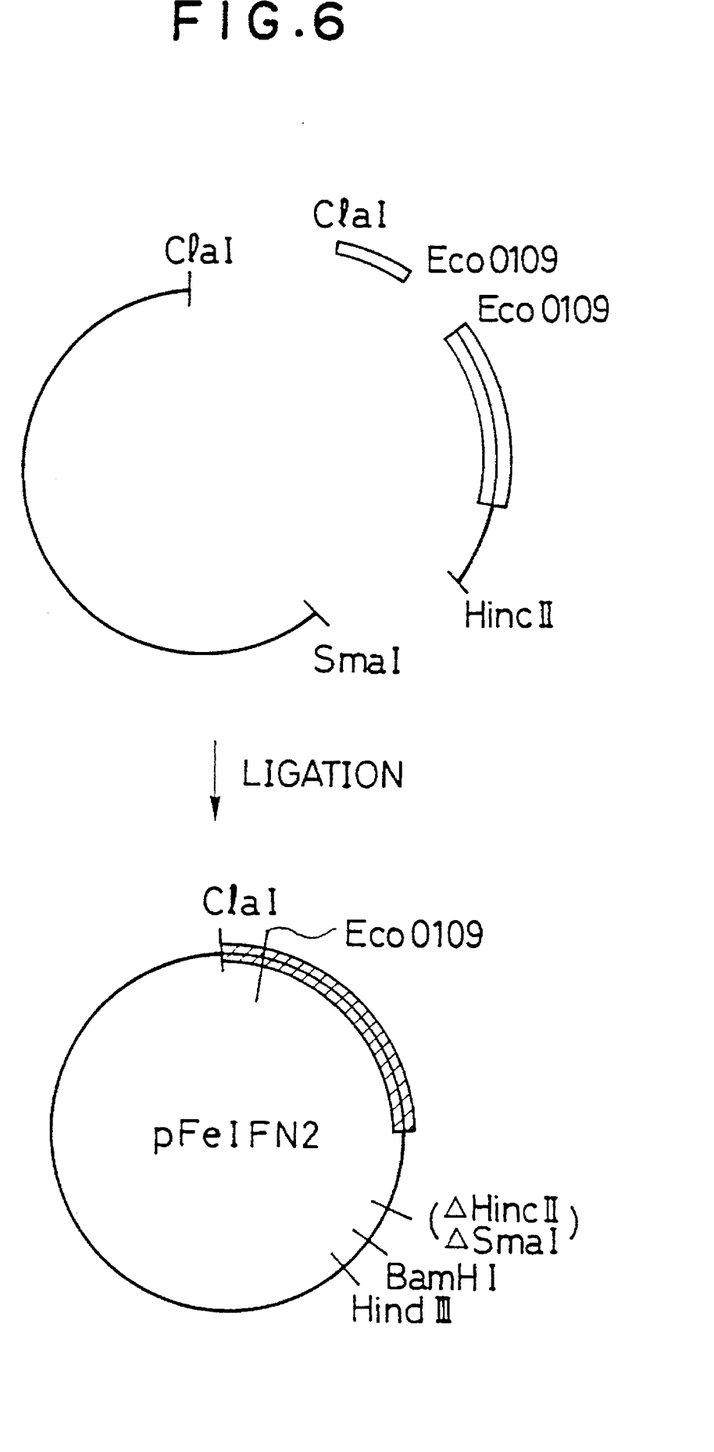

As shown in FIG. 6, the ligation with T4-DNA ligase was carried out by using 3 DNA fragments obtained in the above (1), (3) and (4). Here, the ligation was possible because the SmaI and the HincII ends are both blunt ends. The reaction solution was mixed with E. coli MC1061 which was made to be competent to carry out the transformation reaction. Clones grown in an LB plate containing 100 μg/ml ampicillin were incubated overnight at 37° C. in 2 ml of LB medium containing 100 μg/ml ampicillin. From the culture, plasmids were extracted according to alkaline miniscreen method. The extracted plasmids were digested with ClaI and HindII to screen for clones in which DNA fragments having the desired size were integrated. 3 clones were selected from among the obtained clones and subjected to DNA sequencing with respect to approx. 150 bases containing ClaI-Eco0109 fragments to confirm that the desired plasmids were obtained.

(6) Expression of Plasmid pFeIFN2

The strain HB101 transformed with plasmid pFeIFN2 was incubated in 10 ml of LB medium containing 100 μg/ml ampicillin at 30° C. for 8 hours. Then, the culture was diluted in 50 ml of 2×M9 medium (0.6% $KH_2PO_4$, 1.2% $Na_2HPO_4$, 0.2% $NH_4Cl$, 0.1% NaCl, 1% casamino acid, 1% glucose, 0.25 μg/ml $MgSO_4.7H_2O$, 0.01 μg/ml thiamine) at the inoculum size 5% and aerobically incubated overnight at 25° C. When the $OD_{550}$ reached 8 to 10 and then 1% glucose was added to the medium, the pH of the medium was adjusted to 7.0 and 20 μg/ml indoleacrylic acid was added thereto. After an 8-hour cultivation, cells were harvested and lysed by freeze-thawing and lyzozyme treatment and the lysate was subjected to centrifugation to remove cell debris. As a result of determining the anitviral activity of the supernatant, it was found that $1.2 \times 10^4$ unit/ml (culture medium) of FeIFN was produced.

EXAMPLE 3

Determination of cDNA Base Sequence of FeIFN

Figure 8:
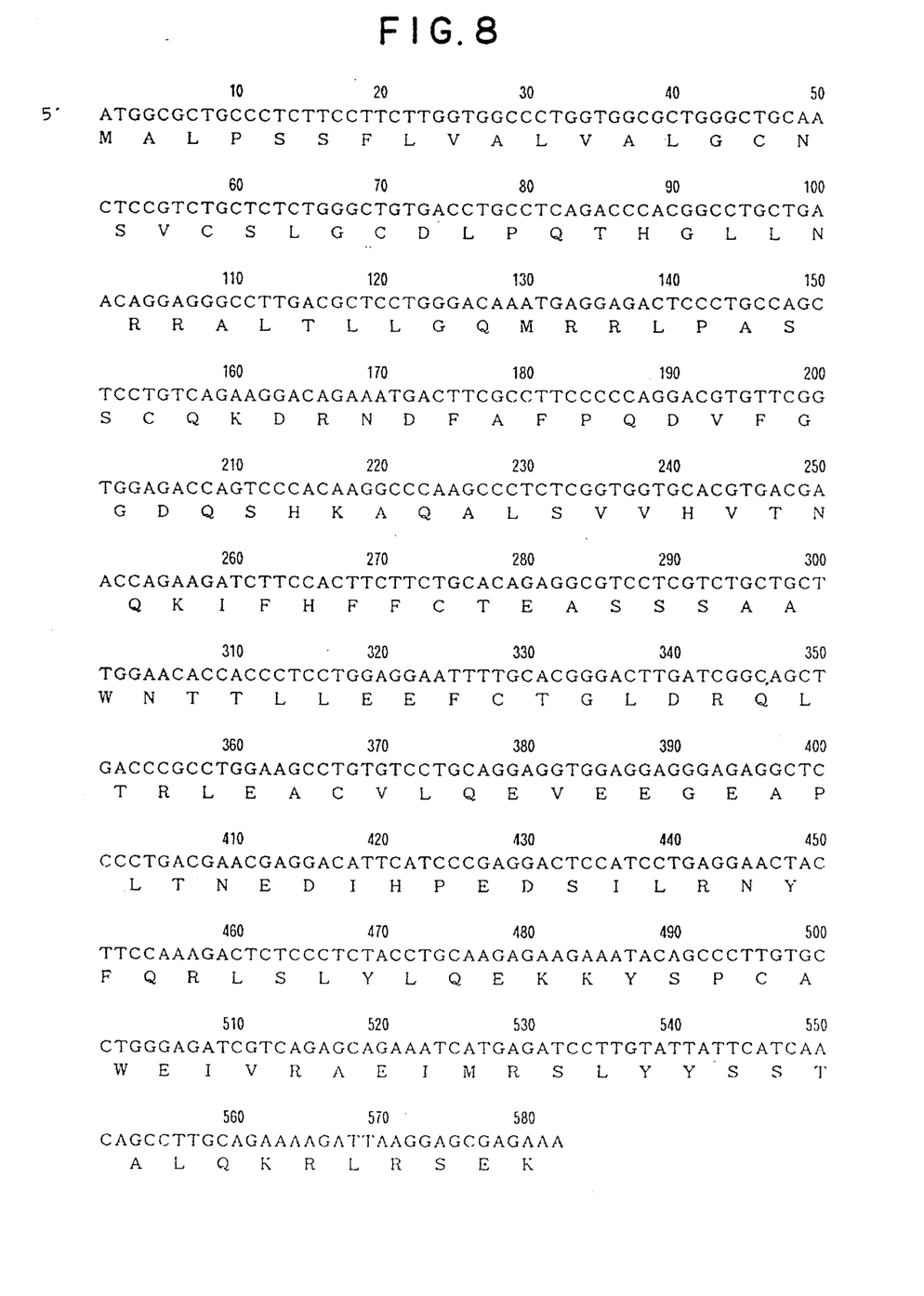

A BamHI fragment isolated from the pFeIFN1 was inserted into a sequencing vector pUC 18 (manufactured by Takara Shuzo Co., Ltd.). In the thus processed vector, the nucleotide sequence, the FeIFN cDNA was determined by the dideoxy sequencing method using a 7-DEAZA sequencing kit (manufactured by Takara Shuzo Co., Ltd.). Parts having indiscernible autoradiographic bands were confirmed according to Maxam-Gilbert method. Whereby, the DNA base sequence shown in FIG. 8 was determined.

EXAMPLE 4

After proliferating COS1 cells in 20 ml of RPMI1640 medium (manufactured by GIBCO inc.) containing 10% FBS in a 15 cm petri dish so that the dish might become confluent, the medium was removed therefrom and then 4 ml of RPMI1640 medium containing 7.5 μg/ml plasmid pFeIFN1 obtained in Example 1, 50 mM Tris-HCl buffer (pH 7.4) and 300 μg/ml DEAE-dextran (manufactured by Pharmacia Inc.) was poured into the dish to continue the incubation at 37° C. for 4 hours. Then, the medium was changed with 4 ml of RPMI1640 medium containing 150 μM chloroquine. After continuing the incubation at 37° C. for 3 hours, the medium was changed with a RPMI1640 medium containing 10% FBS and the incubation was continued at 37° C. for 3 days. All of the above RPMI1640 media were used by adding thereto 100 unit/me penicillin and 100 μg/ml streptomycin.

After the completion of the incubation, the supernatant was obtained. This crude FeIFN solution contained the FeIFN activity of $2.6 \times 10^4$ U/ml and had the specific activity of $2.3 \times 10^4$ U/mg protein. 18 L of this solution was loaded to a column containing 500 ml of Blue Sepharose (fast flow type). After washing the column with 5 L of 50 mM phosphate buffer (pH 7.0) containing 0.5M sodium chloride, the adsorbed FeIFN was eluted with 0.5 L of 50 mM phosphate buffer (pH 7.0) containing 1M sodium chloride and 1.0 l of 50 mM phosphate buffer (pH7.0) containing 1M sodium chloride and 20% ethylene glycol. The eluted FeIFN contained the FeIFN activity of $2.3 \times 10^5$ U/ml and had the specific activity of $2.8 \times 10^6$ U/mg protein. The recovery of FeIFN activity reached 75% and the specific activity was raised by 121-fold.

Then, 1.5 l of FeIFN eluate from the blue carrier was directly loaded to a column containing 70 ml of Sepharose chelated with copper. After washing this column with 20 mM acetate buffer (pH 3.9) containing 0.5M sodium chloride, the adsorbed FeIFN was eluted with 210 ml of 20 mM acetate buffer (pH 3.6) containing 0.5M sodium chloride. The eluted FeIFN contained the FeIFN activity of $1.2 \times 10^6$ U/ml and had the specific activity of $7.1 \times 10^7$ U/mg protein.

The recovery of FeIFN activity reached 77% and the specific activity was raised by 23-fold.

Furthermore, 210 ml of FeIFN eluate from the copper chelate carrier was loaded to a column containing 15 ml of Red Sepharose (fast flow type). After washing this column with 200 ml of phosphate-buffered saline solution (pH 7.0), the adsorbed FeIFN was eluted with 15 ml of 50 mM phosphate buffer (pH 7.0) containing 1M sodium chloride and 40% ethylene glycol. The eluted FeIFN contained the FeIFN activity of $2.0\times10^7$ U/ml and had the specific activity of $5.9\times10^8$ U/mg protein. The recovery of FeIFN activity reached 95% and the specific activity was raised by 11-fold. The total increase in specific activity obtained by the purification is >30,000-fold.

REFERENTIAL LITERATURES

1. Shigeyasu Kobayashie (ed.), 1985. Science of Interferon, Kodansha Scientifics. Kodansha, Tokyo.

2. Official Gazette or. Jap. Pat. Appln. Laid-open No. 224690/1983.

3. Official Gazette of Jap. Pat. Appln. Laid-open No. 501469/1987.

4. A. J. Liberson and A. J. Spillores, 1987. Spectrum, Feb. 1-21-1-23. In Arthur D. Little's Decision Resources, U.S.A.

5. J. K. Yamamoto et al, 1986. *Vet. Immunol. and Immunopathol.* 11, pp. 1–9

6. N. Pedersen et al, 1987. *Science* 235, pp. 790– 793.

7. Shinichiro Konishi, 1985. Vital Diseases of Dogs and Cats. Gakusousha, Tokyo.

8. V. P. Steed, 1987. *Feline Practice* 17, pp. 24–30.

9. T., Maniatis et al (eds.), 1982. Molecular Cloning, A Laboratory Manual. Cold Spring Harbor Laboratory, New York.

10. The Japanese Biochemical Society (eds.), 1986. Genetic Research Method II in Lectures on Biochemical Experiment, 2nd series, vol. 1. Tokyo Kagakudojin, Tokyo.

11. The Japanese Biochemical Society (eds.), 1987. Genetic Research Method III in Lectures on Biochemical Experiment, 2nd series, vol. 1. Tokyo Kagakudojin, Tokyo.

12. The Japanese Biochemical Society (eds.), 1987. Lectures on Biochemical Experiment, 2nd series, vol. 5, pp. 250–256. Tokyo Kagakudojin, Tokyo.

13. F. L. Grabam et al, (1973). *Virology* 54, pp. 536–.

14. Pages 221–236 of Literature 11.

15. Katsuya Shigesada, 1983. *Saibo Kogaku* (Cell Technology) 2, pp. 616–629.

16. M. J. Casadaban et al., 1980. *J. Mol. Biol.* 138, pp. 179–207.

17. Pages 86–96 of Literature 9.

18. G. Urlaub and L. A. Chasin, 1980. *ProNAS,* 77, pp. 4216–4220.

19. Y. Gluzman, 1981. *Cell,* 23, pp. 175–182.

20. R. J. Kaufman and P. A. Sharp, 1982. *Mol. Cell. Biol.* 2, pp. 1304–1319.

Figure 7:
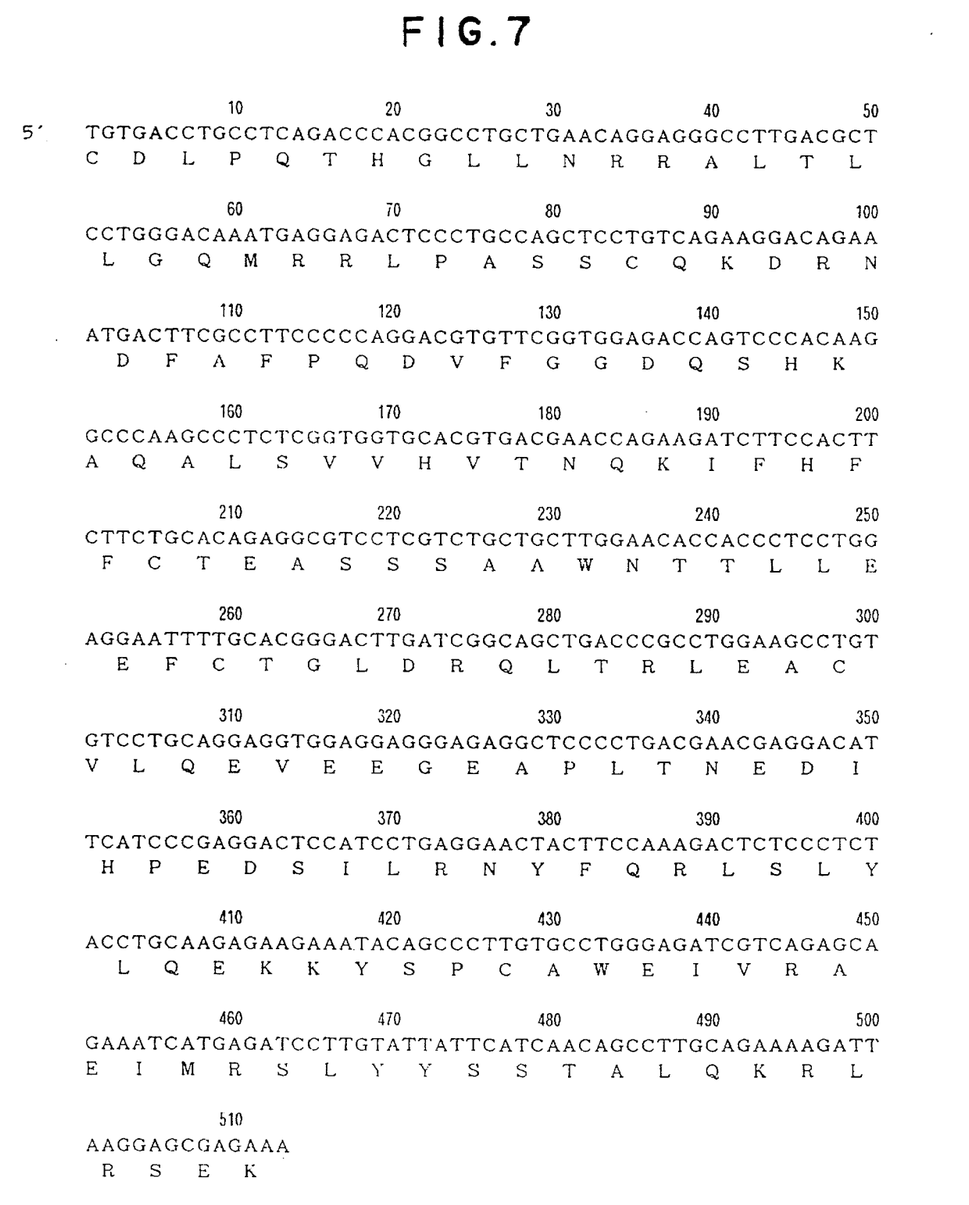
FIG. 7 shows a gene sequence and an amino acid sequence of a feline IFN, and, FIG. 8 shows a gene sequence and an amino acid sequence of a feline IFN precursor.

What is claimed is:

1. A purified, isolated feline interferon comprising a polypeptide having the amine acid sequence set forth in FIG. 7 and having a specific activity ranging from $1.3\times10^6$ to $2.7\times10^8$ units per mg of protein.

2. A feline interferon of claim 1, which further comprises a sugar chain.

3. A purified, isolated feline interferon comprising a polypeptide having the amino acid sequence set forth in FIG. 8, and having a specific activity ranging from $2.8\times10^6$ to $5.9\times10^8$ units per mg of protein.

4. A feline interferon of claim 3, which further comprises a sugar chain.

* * * * *